United States Patent [19]
Hayden

[11] Patent Number: 4,820,260
[45] Date of Patent: Apr. 11, 1989

[54] METHOD AND APPARATUS FOR EXTRAVASCULAR TREATMENT OF RED BLOOD CELLS

[76] Inventor: Steven M. Hayden, 2105 Canterburry Rd., Alexander City, Ala. 35010

[21] Appl. No.: 118,763

[22] Filed: Nov. 9, 1987

Related U.S. Application Data

[63] Continuation-in-part of Ser. No. 928,563, Nov. 10, 1986, abandoned.

[51] Int. Cl.⁴ .................... A61M 37/00; A61H 1/00
[52] U.S. Cl. .................................... 604/4; 128/24 A
[58] Field of Search ............................. 604/4–6; 128/24 A

[56] References Cited

U.S. PATENT DOCUMENTS

| | | | |
|---|---|---|---|
| 3,237,623 | 3/1966 | Gordon | 128/24 A |
| 3,499,437 | 3/1970 | Balamuth | 128/24 |
| 3,565,062 | 2/1971 | Kuris | 128/24 |
| 3,626,218 | 12/1971 | Shriver | 128/24 A |
| 3,674,010 | 7/1972 | Goldberg | 128/24 A |
| 3,777,740 | 12/1973 | Hokanson | 128/24 A |
| 3,867,929 | 10/1975 | Joyner et al. | 128/24 A |
| 3,941,122 | 3/1976 | Jones | 128/24 A |
| 4,315,514 | 2/1982 | Drewes et al. | 128/24 A |
| 4,484,564 | 11/1984 | Driller et al. | 128/24 A |
| 4,549,533 | 10/1985 | Cain et al. | 128/24 A |
| 4,651,716 | 3/1987 | Forester et al. | 128/24 A |

FOREIGN PATENT DOCUMENTS

| | | | |
|---|---|---|---|
| 85/03634 | 8/1985 | PCT Int'l Appl. | 128/24 A |
| 468632 | 9/1975 | U.S.S.R. | 122/24 A |
| 0770496 | 10/1980 | U.S.S.R. | 128/24 A |

OTHER PUBLICATIONS

Pinamonti et al., "Effect of Pulsed Ultrasound On Human Erythrocytes in Vitro", *Ultrasound in Medicine and Biology,* vol 8, No. 6, pp. 631–638, 1982.

Khalil Wakim, "Ultrasonic Energy as Applied to Medicine", *Review of Physical Medicine and Rehabilitation,* pp. 32–45.

Howard Alliger, "Ultrasonic Disruption", *American Laboratory,* vol. 7, No. 10 (Oct. 1975), 75–76, 78, 80–82, 84, 85.

*Primary Examiner*—C. Fred Rosenbaum
*Assistant Examiner*—Kathleen Daley
*Attorney, Agent, or Firm*—Jennings, Carter, Thompson & Veal

[57] ABSTRACT

A method and apparatus for sonication of blood to reduce Na+K+ ATPase activity utilizes an extravascular sonication chamber and a blood pump to control the sonication parameters to prevent morphological damage to the blood cells. Secondary damage to surrounding tissues is avoided by sonicating the blood externally of the body. The sonicated blood may either be stored or returned directly to the body.

14 Claims, 1 Drawing Sheet

METHOD AND APPARATUS FOR EXTRAVASCULAR TREATMENT OF RED BLOOD CELLS

This is a continuation-in-part of Ser. No. 928,563 filed Nov. 10, 1986, now abandoned.

FIELD OF THE INVENTION

The present invention relates to processes and apparatus for treatment of red blood cells through the use of ultrasound. More particularly, the present invention relates to treatment of red blood cells removed from the vascular system with ultrasound at subcavitation inducing levels to inactivate the sodium potassium ATPase of red blood cells.

BACKGROUND OF THE INVENTION

The utilization of ultrasonic energy in medical applications is widespread and is received with varying degrees of enthusiasm and skepticism. As early as 1953, Kholil Wakim reported observations of the European experience with ultrasound in the *Review of Physical Medicine and Rehabilitation*, "Ultrasonic Energy as Applied to Medicine", Feb. 1953, pp 32–45. Wakim punctuated the fantastic claims of the European community with the sobering call for investigation of the adverse effects of ultrasound treatments. The mechanism of cellular sonication has further been reported by Howard Alligor in *American Laboratory*, "Ultrasonic Disruption" in October 1975 at pp. 75 et seq. Alligor postulated the release of enzymes and protein from cells and subcellular particles as an outstanding application of ultrasonics. Pinamonti et al reported in *Ultrasound in Medicine and Biology*, "Effect of Pulsed Ultrasound on Human Erythrocytes In Vitro", Vol 8, No. 6, pp. 631–638 (1982) that sonication of the red blood cells resulted in the disappearance of sodium potassium ATPase activity in the cells. Numerous patent references cite the use of ultrasound in medical treatments. Yet no teaching is known by the inventor wherein a specific treatment method or apparatus has been suggested for sonication of body cells outside the body for subsequent assimilation into the body.

SUMMARY OF THE INVENTION

It is the object of this invention to provide a method and apparatus for sonication of red blood cells externally of the body to cause chemical change in such cells and re-introduction of the red blood cells to the body in a sonicated state.

A further object of the invention is to alter the $O_2$ affinity of the red blood cells to improve the oxygen transport qualities thereof.

Still another object of the invention is to enable sonication of the selected blood cells without ultrasonic damage to the tissues surrounding the vascular system.

Yet another object of the invention is to reduce the incidence of sickling in the red blood cells.

It should be appreciated that heretofore sonication of the human anatomy has involved sonication of entire organs and the adjacent tissues. As noted herein above sonication can have deleterious effects on tissues and a certain incidence of toxicity is likely to occur in the adjacent tissues or the treated organ itself due such sonication. Further to accomplish the above objects for any useful purpose the sodium potassium ATPase enzyme is inactivated by exposure to relatively high intensities and frequencies of ultrasonic energy. Consequently in the present invention, the red blood cells are first isolated from other tissues, organs, and the circulatory system. Then they are sonicated and returned to the body. In this manner, the ultrasonic parameters can be more closely controlled to avoid morphological damage to the blood and to eliminate such damage to other tissues.

BRIEF DESCRIPTION OF THE DRAWINGS

Apparatus susceptible of use in my invention is depicted schematically in the accompanying drawings which form a portion of this disclosure, wherein.

DESCRIPTION OF THE PREFERRED EMBODIMENT

It is to be understood that red blood cells deliver only about 40% of the oxygen carried thereby while in the capillaries. That is to say that the affinity of the red blood cells for $O_2$ is such that they do not give up 60% of the arterial oxygen content while in the capillary. Pinamonti, referred to above, determined that sonication of the red blood cells resulted in a decreased $O_2$ affinity in such cells, yet the cells retained a good capacity for $O_2$.

Pinamonti also noted that $Na+K+ATPase$ is almost completely inactivated by sonication. Yet Pinamonit's conclusions were that none of his observations had application in medical practice despite these biological effects.

The present method and apparatus are designed to obtain the biological effects suggested by Pinamonti's research and apply them for therapeutic use in medicine. It appears plausible that sonication of red blood cells by virtue of the reduction of the $O_2$ affinity would permit a greater percentage transfer of $O_2$ from the blood in the capillaries. Improvement in the capillary transfer of $O_2$ has a variety of uses in medicine including application to local ischemia, such as peripheral vascular disease, stroke or cerebral vascular disease and/or heart attack, as well as in anemia. Also $Na+K+ATPase$ activity results in low levels of intracellular $Na+$ in the red blood cells. Deactivation of this enzyme results in the retention of $Na+$ salts and hence water in the red cell, therefore the cells do not become dehydrated and sickling of the cells is retarded. From the foregoing, it may be seen that sonication of blood may have very useful therapeutic benefits; however, these benefits are best achieved by extravascular sonication wherein the sonication parameters can be more closely controlled and damage to other tissues can be avoided.

Figure 1:
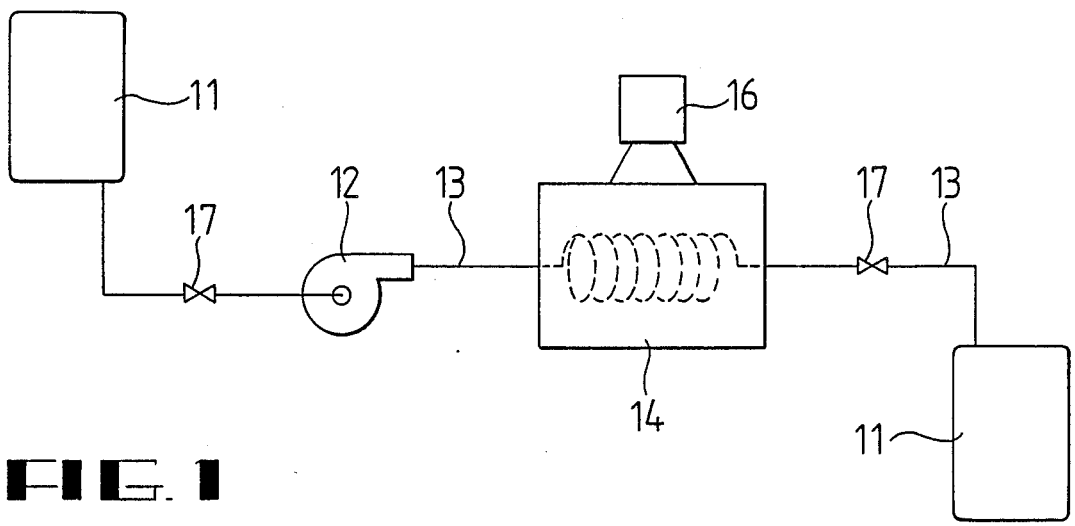
FIG. 1 is a schematic depiction of an embodiment wherein blood drawn from a storage container is sonicated and stored.

In FIG. 1, I present a schematic representation of one embodiment of my invention wherein blood is removed from a storage container 11, which may be a conventional container as is commonly used in hospitals and blood banks, via a blood pump 12, also of conventional design as used in dialysis or the like, through a conduit 13. The conduit 13 which is invisible to transmission of ultrasound energy, passes through an ultrasound chamber 14 which defines a relatively uniform ultrasound field created by one or more ultrasound transducers 16. The transducer 16 may be commercially obtained from a number of vendors and should produce an intensity of between three watts per cm² to 30,000 watts per cm² at a frequency of between 500 Khz and 50 Mhz. The chamber 14 is also well within the realm of knowledge of those familiar with the art of ultrasonic energy control and should be designed such that the field produced by the transducer 16 is generally uniform in at least a region of the field. The conduit 13 may be configured to expose the blood carried therein uniformly within the field for a duration determined by the pump 12. Of couse, all of the materials selected for use must be suitable to avoid promoting thrombosis or hemolysis.

As may be seen the exposure parameters of intensity, frequency, and duration of exposure may be varied to assure that the blood is uniformly sonicated at a level below the cavitation threshold of the blood to avoid morphological damage to the cells. In some instances, increased pressure can help to reduce cavitation effects, thus I provide a set of valves 17 which allow the pressure in the conduit to be raised by the pump 12.

Figure 2:
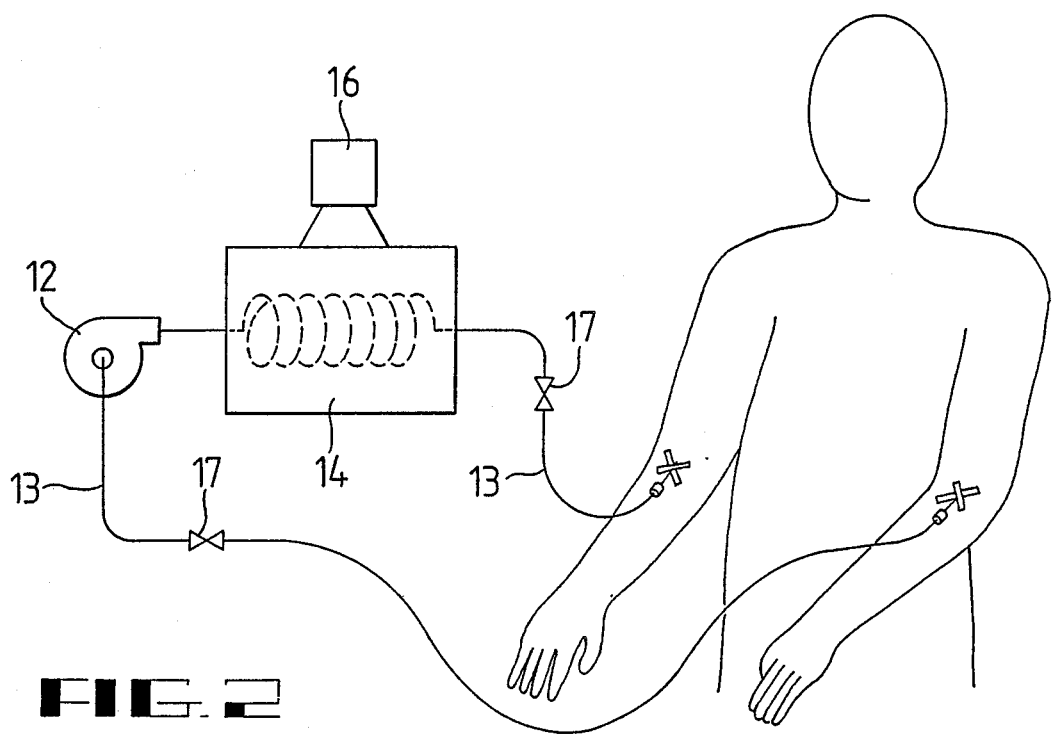
FIG. 2 is a schematic depiction of an embodiment wherein sonicated blood is returned directly to a patient.

These valves are also included in the embodiment shown in FIG. 2 to isolate the circulatory system of a patient undergoing direct treatment of his blood. In FIG. 1, stored blood is sonicated to enhance its $O_2$ carrying properties and then returned to storage to await emergency use. In FIG. 2, it may be seen that the sonicated blood is taken directly from and returned directly to the patient.

In each of the above embodiments, the method of treatment requires utilization of ultrasonic energy to reduce the ATPase activity, thus as a theoretical and practical matter, the exposure, frequency, an intensity used in the method should be defined by the amount necessary for deactivating the ATPase. Such activity is measurable with known technology and thus provides a control and limitation on the use of my method and apparatus in treatment.

While I have shown my invention in various forms, it will be obvious to those skilled in the art that it is not so limited but is susceptible of various changes and modifications without departing from the spirit thereof.

What I claim is:

1. Apparatus for extravascular sonication of red blood cells comprising:
    (a) means for generating an ultrasound field of predetermined strength and frequency within a confined region; and
    (b) extravascular means for exposing red blood cells within said region for a predetermined duration, wherein the parameter of said ultrasound field and the duration of said exposure are such that the cavitational threshold of said red blood cells is not reached during treatment including a blood pump and conduit means passing through said ultrasonic field from said blood pump with said conduit means being transmissive to said ultrasound field.

2. Apparatus as defined in claim 1 wherein said field has a predetermined peak strength of from about 3 watt/cm² to about 30,000 watts/cm² and a frequency of between about 500 kilohertz and about 50 megahertz.

3. Apparatus as defined in claim 2 wherein said field is pulsed.

4. Apparatus as defined in claim 1 wherein said field is pulsed.

5. Apparatus as defined in claim 1 further comprising means for collecting sonicated blood from said means for transporting.

6. Apparatus as defined in claim 1 wherein said extravascular means further comprises:
    (a) means for withdrawing blood from the circulatory system of a patient;
    (b) means for returning sonicated blood from said conduit means to said patient's circulatory system; and
    (c) means for isolating the circulatory system of said patient from any excessive pressures generated by said apparatus.

7. Apparatus for extravascular sonication of red blood cells comprising:
    (a) means for generating an ultrasound field of predetermined strength and frequency within a confined region including an ultrasound chamber within which said ultrasonic field may be confined and at least one transducer capable of creating an ultrasonic field within said chamber; and
    (b) extravascular means for exposing red blood cells within said region for a predetermined period wherein the parameters of said ultrasound field and the duration of said exposure are such that the cavitational threshold of said red blood cells is not reached during treatment, including means for storing unsonicated blood and means for transporting blood from said means for storing including a blood pump and conduit means passing through said ultrasound field from said pump with said conduit means being transmissive to said ultrasound field.

8. Apparatus for extravascular sonication of red blood cells comprising:
    (a) means for generating an ultrasound field of predetermined strength and frequency within a confined region; and
    (b) extravascular means for exposing red blood cells within said region for a predetermined period wherein the parameters of said ultrasound field and the duration of said exposure are such that the cavitational threshold of said red blood cells is not reached during treatment, including means for storing unsonicated blood, and means for transporting blood from said means for storing comprising a blood pump and conduit means passing from said blood pump through said ultrasound field with said conduit means being transmissive to said ultrasound field.

9. A method of treating red blood cells with ultrasound comprising:
    (a) removing a quantity of blood to be treated from the circulatory system of a person;
    (b) creating within a defined region outside the patient's body an ultrasound field having predetermined parameters of intensity and frequency;
    (c) exposing the quantity of blood within said field for a predetermined duration with said field intensity and frequency and said duration of exposure controlled to prevent cavitaton in the blood during sonication thereof; and
    (d) introducing the sonicated blood into the circulatory system of a person.

10. The method as defined in claim 9 wherein said field has a predetermined peak strength of from about 3 watt/cm² to about 30,000 watts/cm² and a frequency of between about 500 kilohertz and about 50 megahertz.

11. The method as defined in claim 9 wherein said field is pulsed.

12. The method as defined in claim 9 wherein said blood is stored before sonication.

13. The method as defined in claim 9 wherein said blood is stored after sonication.

14. The method as defined in claim 9 wherein said field parameters and said exposure are controlled such that said sonication is of sufficient extent to uniformly inactivate the sodium potassium ATPase of the red blood cells without inducing morphological damage therein.

* * * * *